United States Patent
Baseeth et al.

(10) Patent No.: US 10,384,178 B2
(45) Date of Patent: Aug. 20, 2019

(54) MICROEMULSIONS AND USES THEREOF AS NANOREACTORS OR DELIVERY VEHICLES

(71) Applicant: ARCHER DANIELS MIDLAND COMPANY, Decatur, IL (US)

(72) Inventors: Shireen Baseeth, Decatur, IL (US); Swapnil Jadhav, Decatur, IL (US)

(73) Assignee: Archer Daniel Midland Company, Decatur, IL (US)

( * ) Notice: Subject to any disclaimer, the term of this patent is extended or adjusted under 35 U.S.C. 154(b) by 0 days.

(21) Appl. No.: 14/405,805

(22) PCT Filed: Jun. 28, 2013

(86) PCT No.: PCT/US2013/048588
§ 371 (c)(1),
(2) Date: Dec. 5, 2014

(87) PCT Pub. No.: WO2014/005029
PCT Pub. Date: Jan. 3, 2014

(65) Prior Publication Data
US 2015/0151264 A1    Jun. 4, 2015

Related U.S. Application Data

(60) Provisional application No. 61/666,378, filed on Jun. 29, 2012.

(51) Int. Cl.
| | | |
|---|---|---|
| *B01F 17/00* | (2006.01) | |
| *A61K 8/11* | (2006.01) | |
| *A61Q 9/00* | (2006.01) | |
| *A61K 8/49* | (2006.01) | |
| *A61K 8/365* | (2006.01) | |
| *A61K 9/107* | (2006.01) | |
| *C09K 8/035* | (2006.01) | |
| *A61K 8/55* | (2006.01) | |
| *A61K 8/06* | (2006.01) | |
| *A61K 47/24* | (2006.01) | |
| *A61Q 19/00* | (2006.01) | |

(52) U.S. Cl.
CPC .......... *B01F 17/0064* (2013.01); *A61K 8/068* (2013.01); *A61K 8/11* (2013.01); *A61K 8/365* (2013.01); *A61K 8/4993* (2013.01); *A61K 8/553* (2013.01); *A61K 9/1075* (2013.01); *A61K 47/24* (2013.01); *A61Q 19/00* (2013.01); *C09K 8/035* (2013.01); *A61K 2800/10* (2013.01); *A61K 2800/413* (2013.01); *C09K 2208/10* (2013.01)

(58) Field of Classification Search
None
See application file for complete search history.

(56) References Cited

U.S. PATENT DOCUMENTS

| | | | | |
|---|---|---|---|---|
| 5,698,138 | A * | 12/1997 | Visca ................. | B01F 17/0035 508/582 |
| 2006/0008498 | A1* | 1/2006 | Chen ............................ | 424/422 |
| 2007/0078057 | A1* | 4/2007 | Rowley ................. | A01N 25/04 504/206 |
| 2007/0087104 | A1* | 4/2007 | Chanamai ..................... | 426/602 |
| 2008/0139392 | A1* | 6/2008 | Acosta-Zara ........ | A61K 9/0014 504/359 |
| 2010/0233275 | A1* | 9/2010 | Saulnier et al. .............. | 424/490 |
| 2012/0015004 | A1* | 1/2012 | Mironov et al. .............. | 424/400 |

FOREIGN PATENT DOCUMENTS

| | | | | |
|---|---|---|---|---|
| WO | WO-2011117333 | A2 * | 9/2011 | .......... A61K 9/1075 |
| WO | WO 2012068105 | A2 * | 5/2012 | |

OTHER PUBLICATIONS

Antonietti et al. Langmuir 1994 10:2498-2500.*
Dielectric Constants reference www.engineeringtoolbox.com/liquid-dielectric-constants-d_1263. html Jul. 2011.*
Trotta et al. International Journal of Pharmaceutics 2003 254:235-2420.*
Simmons et al. Nano Letters 2002 2(4):263-268.*
Trotta Journal of Controlled Release 1999 60:399-405.*
Wang et al. Materials Research Bulletin 2000 35:53-58.*
Bezbaruah et al. Journal of Hazardous Materials 2009 166:1339-1343.*
Zech et al. Nonaqueous Microemulsions Containing Ionic Liquids—Properties and Applications, Ionic Liquids: Theory, Properties, New Approaches, Kokorin (Ed.), 2011, p. 245-270, Available from: www.intechopen.com/books/ionic-liquids-theoryproperties-new-approaches/nonaqueous-microemulsions-containing-ionic-liquids-properties-and-applications.*
Malik et al. Arabian Journal of Chemistry 2012 5: 397-417.*
Ralston et al. Journal of Organic Chemistry 1942, 7(6): 546-555.*
Hammond et al. "Soybean oil" in Bailey's Industrial Oil and Fat Products, Sixth Edition. Shahidi ed. John Wiley & Sons:Hoboken, 2005 p. 577-653.*
Crane et al. Water Research 2011 45:2931-2942 (Year: 2011).*
Yuan et al. International Journal of Pharmaceutics 2008 349:130-143 (Year: 2008).*

* cited by examiner

*Primary Examiner* — Robert A Wax
*Assistant Examiner* — Caralynne E Helm
(74) *Attorney, Agent, or Firm* — Andrew F. Nilles

(57) ABSTRACT

Lecithin based microemulsion and their uses as nanoreactors and carrying materials are disclosed. In one embodiment, a method of forming a nanomaterial comprises mixing a lecithin based microemulsion with a first reactant and a second reactant. In a further embodiment, a method for encapsulating a nanomaterial in a lecithin based microemulsion forming a composition and wherein the composition forms a dispersion in an aqueous solution, polar solution, or a non-polar solution.

6 Claims, No Drawings

MICROEMULSIONS AND USES THEREOF AS NANOREACTORS OR DELIVERY VEHICLES

CROSS-REFERENCE TO RELATED APPLICATIONS

This application is a national stage entry of International Application No. PCT/US13/48588, filed Jun. 28, 2013, which itself claims priority to U.S. Provisional Patent Application No. 61/666,378, filed Jun. 29, 2012, each of the contents of the entirety of which are incorporated by this reference.

TECHNICAL FIELD

The present invention relates generally to microemulsions. More particularly, the present invention relates to uses of lecithin microemulsions as nanoreactors or to carry nanomaterials.

BACKGROUND OF THE INVENTION

Nature employs different types of cells to perform routine chemical, reactions in a living organism. By virtue of nano-size compartmentalization and reactant selectivity, a cell can perform cascades of complex reactions with extreme precision and spatial control. A man-made or artificial reaction system which attempts to mimic the proficiency of biological reactors in cells are referred to as nanoreactors. A nanoreactor is typically a compartment that is smaller than one micron in size and that encloses an environment where a reaction may take place in a controlled and well defined manner.

Nanoreactors have been used to develop nanomaterials such as nanoparticles (i.e., metals, metal oxides, metal alloys, metal coated metal oxide, metal oxide coated metal), ceramic materials, and quantum dots. In comparison to their bulk or larger counterparts, nanomaterials exhibit different optical, magnetic, electrical, physical (i.e., mechanical hardness, thermal stability, and chemical passivity), and catalytic properties which may provide different uses of such nanomaterials.

By using principles of self-assembly, various types of nanoreactors have been developed from synthetic and biological building blocks. Examples of such nanoreactors include emulsions, microemulsions. micelles, gels, protein cages, and viruses. The microemulsions (µE) are an efficient system and are clear, thermodynamically stable, colloidal nanodisperions of water in oil or oil in water. The dispersed phase is stabilized within micelles formed by self-assembly of surfactants. Due to Brownian motion, the micelles frequently collide and transiently fuse leading to an exchange of the components within the interior of the micelle. Such dynamic properties facilitate the use of the micelles as confined reaction media and, thus, their utility as nanoreactors.

Advantages of using microemulsions as nanoreactors include: accelerating the rate of reaction up to 100 fold; imparting a cage-like effect which provides good control over particle size which produces particle/nanomaterials with high homogeneity and monodispersity; the surfactant film on the micelles stabilizes the particles and prevents the particles from agglomerating; and the ease of manipulating the properties of the microemulsions enables the fine-tuning of the size and morphology of the nanomaterials.

Water in oil microemulsions have been widely used to produce nanoparticles. However, most of the microemulsions use surfactants that are not biodegradable (i.e., Aerosol OT. Triton X-100, and polyvinylpyrrolidone) and use organic solvents that are hazardous and petroleum based (i.e., iso-octane, heptane, and 1-butanol).

Nanofluids are a class of colloidal systems developed by uniformly dispersing nanomaterials (i.e., nanoparticles, nanofibers, nanotubes, nanowires, nanorods, nanosheets, or nanodroplets) in base fluids. As compared to the base fluids themselves, the nanofluids have different properties such as enhanced thermal conductivity, thermal diffusivity, thermal viscosity, and hear transfer coefficients. Due to the improved thermophysical properties, the nanofluids may be used for applications such as heat transfer, mass transfer, energy storage, tribological uses, and biomedical uses. Nanofluids are categorized as water-based or oil-based. The water-based fluids may be exploited for heat transfer and the oil-based nanofluids may be used in lubricant applications. However, dispersing nanoparticles into oils to make such nanofluids is a challenge and nanofluids are not very stable since nanoparticles often aggregate and precipitate after a few days.

Pure phospholipids such as phosphatidylcholine have been used as a biobased surfactant to produce nanoreactors such as vesicles and liquid crystals. However, lecithin, which is a complex mixture including phospholipids, has not been used to develop nanoreactors. Pure phospholipids are about ten times more expensive than lecithin.

SUMMARY OF THE INVENTION

In each of its various embodiments, the present invention fulfills these needs and discloses lecithin based microemulsions and their uses as nanoreactors and carrying materials.

In one embodiment, a method of forming a nanomaterial comprises mixing a lecithin based microemulsion with a first reactant and a second reactant.

In another embodiment, a composition comprises a lecithin based microemulsion, a first reactant, and a second reactant.

In a further embodiment, a method of encapsulating a nanomaterial in a lecithin based microemulsion comprises mixing the lecithin based microemulsion with the nanomaterial, thus encapsulating and stabilizing the nanomaterial.

In an additional embodiment, a composition comprises a lecithin based microemulsion and a nanomaterial. The composition forms a dispersion in an aqueous solution, a polar solution, or a non-polar solution.

DETAILED DESCRIPTION OF THE INVENTION

Work on microemulsions and uses thereof have continued. International Patent Application PCT/US13/29129 entitled "Electrolyte and pH Stable Lecithin Compositions," assigned to Archer-Daniels-Midland Company, discloses the production of microemulsions and uses thereof, the contents of the entirety of which is incorporated by this reference. WO 2012/068105 discloses the production of microemulsions and uses thereof, the contents of the entirety of which is incorporated by this reference. The present application discloses microemulsions and uses thereof as nanoreactors, as carrying nanomaterials or in nanofluids.

In the present application, including the claims, other than in the operating examples or where otherwise indicated, all numbers expressing quantities or characteristics are to be understood as being modified in ail instances by the term "about". Unless indicated to the contrary, any numerical parameters set forth in the following description may vary depending on the desired properties in the compositions and methods according to the present disclosure. At the very least, and not as an attempt to limit the application, of the doctrine of equivalents to the scope of the claims, each numerical parameter described in the present description should at least be construed in light of the number of reported significant digits and by applying ordinary rounding techniques.

Any patent, publication, or other disclosure material in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

In one embodiment, a method of forming a nanomaterial comprises, mixing a lecithin based microemulsion with a first reactant and a second reactant. The interaction between the first reactant and the second reactant produces the nanomaterial. The lecithin based microemulsion may be mixed with the first reactant before mixing with the second reactant. The second reactant may also be mixed with a lecithin based microemulsion before mixing the first reactant and the second reactant. The lecithin based microemulsion may be mixed with the second reactant before mixing with the first reactant. The first reactant may also be mixed with a lecithin based microemulsion before mixing the first reactant and the second reactant. The method may also include mixing the lecithin based microemulsion with the first reactant to produce a first microemulsion, mixing the lecithin based microemulsion with the second reactant to produce a second microemulsion, and mixing the first microemulsion with the second microemulsion. Such, method may simultaneously encapsulate the nanomaterial in the lecithin based microemulsion upon production of the nanomaterial.

In another embodiment, a composition comprises a lecithin based microemulsion, a first reactant, and a second reactant. At least one of the first reactant and the second reactant may be a catalytic agent selected from the group consisting of a reducing agent, an oxidizing agent, metal catalyst, co-enzyme, ligand chelator, and an enzyme. At least one of the first reactant and the second reactant may also be selected from the group consisting of metal salts, metal oxides, metal alloys, metal composites, monomers for polymeric synthesis, oligomers for polymeric synthesis, proteins, and combinations of any thereof. The composition may also biobased. At least one of or both of the first reactant and the second reactant may be encapsulated in the lecithin based microemulsion.

The nanomaterial may have a particle size of 2-500 nanometers (nm), a particle size of 2-250 nm, a particle size of 2-100 nm, a particle size of 5-100 nm, or a particle size of 2-50 nm. The nanomaterial within the lecithin based microemulsion may have a particle size of between 5-50 nm. The lecithin based microemulsion may comprise lecithin, a co-surfactant, and an acidifier selected from the group consisting of a carboxylic acid, a salt of a carboxylic acid, an ester of a carboxylic acid, and combinations of any thereof. The lecithin based microemulsion may further comprise isolated or purified fatty acids. The co-surfactant may be polysorbate. The acidifier may be the carboxylic acid, the salt of the carboxylic acid, and the ester of the carboxylic acid, and the carboxylic acid may be lactic acid. The nanomaterial may be present at a concentration of 0.01-20% by weight.

The first reactant may be selected from the group consisting of metal salts, metal alloys, metal composites, proteins, monomers for polymeric synthesis, oligomers for polymeric synthesis, and combinations of any thereof. The first reactant may be a metal salt having a concentration of between about 0.1 M to about 3M.

The second reactant may be a catalytic agent and may be selected from the group consisting of a reducing agent, an oxidizing agent, an enzyme, co-enzyme, metal catalyst, ligands, chelators, and combinations of any thereof. The reducing agent, may be selected from the group consisting of sodium borohydride, sodium citrate, green tea extract, a polyphenol, a polyphenol derivative, a catechin, a flavonoid, a flavanol a tannin, a lignin, and combinations of any thereof. The method may further include dispersing the lecithin in a solvent having a dielectric constant of between 2-80 or with a non-polar solvent selected from the group consisting of non-polar organic solvents, ionic liquids, vegetable oil, mineral oil, an essential oil, paraffin, petroleum fractions, and combinations of any thereof. The catalytic agent may be present at a concentration of between 0.01-25% by weight.

In one embodiment, a lecithin-based nanoreactor is disclosed. The lecithin-based nanoreactor may include a catalytic agent for catalyzing a reaction, reducing a compound, or oxidizing a compound. The lecithin-based nanoreactor may comprise a lecithin based microemulsion having a reducing agent, an oxidizing agent, an enzyme, or other catalyst in the microemulsion which may be used to develop materials in the nanoreactor. In one embodiment, the reducing agent may be an environmentally benign reducing agent such as green tea extract which is biobased and includes polyphenol components that are essential chemicals that reduce precursors to nanomaterials. In another embodiment the lecithin-based nanoreactor may comprise a lecithin based microemulsion having an oxidizing agent in the microemulsion which may be used to develop nanomaterials. In another embodiment, the lecithin based microemulsion may include a catalyst or catalytic agent that facilitates a reaction of a compound. The catalyst may be an oxidizing agent, a reducing agent, an enzyme, co-enzyme, metal catalyst, ligands, chelators, or other compound that facilitates a reaction of a compound.

In another embodiment, the microemulsion may be include a chelator or ligand which may be used in solution to chelate or bind metal from effluents, drilling fluids, waste water treatment, or even as a free radical scavenger in food, cosmetic, or pharmaceutical applications. In another embodiment, the microemulsion may be used with metal particle encapsulated in the microemulsion to scavenge sulphide and stabilize the resultant, metal sulfide suspension, without phase separation of the microemulsion. The pH and electrolyte stability of the microemulsions or the present invention make such scavenging applications especially useful.

In a further embodiment, a composition comprising a lecithin based microemulsion and a nanomaterial is disclosed. The composition forms a dispersion in a polar solution, a non-polar solution, or an aqueous solution. The composition may further comprise a solvent having a dielectric constant of between 2-80, a non-polar solvent, or a polar solvent. The nanomaterial may have a particle size of between about 5-200 nm. The nanomaterial may comprise a metal, metal salts, metal oxides, metalloenzymes, metal oxide composition, metal compounds, activated carbon, carbon nanofibers, carbon nanoplatelets, carbon nanotubes, fullerenes, graphene, graphene nanopowder, graphene nanoplatelets, graphene oxide fullerenes, an organic nutrient, an inorganic nutrient, metal sulfides, metal alloys, metal composites, proteins, polymers, a nanotube, graphene, graphite, a bioactive, a protein, a nutraceutical a pharmaceutical, a food ingredient, and combinations of any thereof. The nanomaterial may be encapsulated within a core of reverse a self-assembled structure comprising the lecithin based microemulsion. The composition may be biobased and may remain stable in a solvent for at least two weeks. The lecithin based microemulsion may include the components as described herein with reference to microemulsions.

In one embodiment, the nanomaterial may comprise metal salts, metal oxides, metalloenzymes, metal oxide composite, metal compounds, metal sulfides, metal alloys, metal composites, activated carbon, carbon nanotubes, carbon nanofibers, carbon nanoplatelets, graphene, graphene nanopowder, graphene nanoplatelets, graphene oxide fullerenes, proteins, polymers, nutrients (organic and inorganic) and combinations of any thereof. In another embodiment, the nanomaterial may be metals and metal alloys selected from the group consisting of but not limited to, silver, aluminum, gold, platinum, boron, cobalt, copper, chromium, iron, molybdenum, manganese, nickel, magnesium, indium, nickel, silicon, tin, tantalum, titanium, tungsten, zinc, nickel-titanium alloy, tin-copper alloy, iron-nickel-cobalt alloy, iron-nickel alloy, iron-chromium, cobalt alloy, copper-zinc alloy, silver-copper alloy, silver-copper alloy, silver-tin alloy, nickel-chromium-cobalt alloy, aluminum-silicon alloy, copper-nickel alloy, copper-indium alloy, copper-indium-gallium alloy, copper-indium-sulfur alloy and combinations of any thereof.

The nanomaterials may also be metal oxide selected from the group consisting of, but not limited to, aluminum oxide, aluminum hydroxide, bismuth oxide, cerium oxide, cobalt (II) oxide, cobalt(III) oxide, cobalt(II, III) oxide, chromium oxide, copper oxide, cuprous oxide, dysprosium oxide, erbium oxide, europium oxide, iron(II) oxide, iron(III) oxide, gadolinium oxide, hafnium oxide, indium oxide, indium hydroxide, lanthanum oxide, magnesium oxide, magnesium hydroxide, magnesium carbonate, molybdenum oxide, manganese oxide, neodymium, oxide, nickel hydroxide, nickel oxide, praseodymium oxide, antimony oxide, silicon oxide, samarium oxide, tin oxide, terbium oxide, titanium oxide (anatase), titanium oxide (rutile), tungsten oxide, yttrium oxide, zinc oxide, zinc carbonate, zirconium oxide, zirconia hydroxide and combinations of any thereof. The nanomaterials may also be a metal oxide composites selected from the group consisting of, but not limited to, antimony tin oxide, zinc oxide-aluminum oxide, barium iron oxide, barium carbonate, barium titanate, cobalt iron oxide, indium tin oxide, manganese iron oxide, nickel iron oxide, nickel zinc iron oxide, nickel cobalt iron oxide, strontium iron oxide, strontium titanate, yttrium aluminate, zinc iron oxide, zinc cobalt iron oxide, zinc manganese iron oxide and combinations of any thereof. The nanomaterials may be metal compounds selected from the group consisting of, but not limited to, aluminum nitride, boron nitride, boron carbide, chromium carbide, chromium carbide, hafnium carbide, lanthanum hexaboride, lanthanum trifluoride, molybdenum carbide, molybdenum disulfide, molybdenum disilicide, niobium carbide, silicon carbide, silicon nitride, tantalum carbide, titanium boride, titanium carbide, titanium nitride, vanadium carbide, tungsten carbide, tungsten carbide cobalt, tungsten disulfide, zirconium diboride, zirconium carbide, zirconium nitride and combination of any thereof.

The compositions of the present invention may be used as a bioremediation composition, a delivery vehicle for a nanomaterials, a biomedical composition, a cosmetic composition, a nanoreactor, a nanofluid, a food ingredient, as a heat transfer fluid, as a transformer fluid, as a coolant additive, a biolubricant, corrosion inhibitors, descalers, additive for marine application, viscosity modifier, lubricant, or drilling additive for oil field application. In such uses, the nanomaterial may be selected from the group consisting of metal, metal salts, metal oxides, metalloenzymes, metal oxide composition, metal compounds, activated carbon, carbon nanofibers, carbon nanoplatelets, carbon nanotubes, fullerenes, graphene, graphene nanopowder, graphene nanoplatelets, graphene oxide fullerenes, an organic nutrient, an inorganic nutrient, metal sulfides, metal alloys, metal composites, proteins, polymers, nutraceutics, pharmaceutics, bioactive and food ingredients.

In a further embodiment, a method of encapsulating a nanomaterial in a lecithin based microemulsion comprises mixing the lecithin based microemulsion with the nanomaterial thus encapsulating the nanomaterial. The method may further include dispersing the lecithin based microemulsion in a solvent having a dielectric constant of between 2-80. The method may further include dispersing the lecithin based microemulsion in a non-polar solvent selected from the group consisting of non-polar organic solvents, ionic liquids, vegetable oil, mineral oil, an essential oil, paraffin, petroleum fractions, and combinations of any thereof. The method may further comprise mixing a first reactant and a second reactant with the lecithin based microemulsion, wherein an interaction between the first reactant and the second reactant forms the nanomaterial. The lecithin based microemulsion may include the components as described herein with reference to microemulsions.

In a further embodiment, the microemulsion of the present invention with or without a nanomaterial may be dispersed or diluted in a liquid. The liquid may be a polar solvent or a non-polar solvent. Polar solvents that may be used include, but are not limited to water, ethyl lactate, or other polar liquids. Non-polar solvents that may be include, but are not limited to, vegetable oil, mineral oil, silicone oil, an essential oil, paraffin, or combinations of any thereof.

In another embodiment, nanomaterials may be produced by dissolving a reactant used to create the nanomaterials in a liquid, such as water. A microemulsion of the present invention may also be dissolved or dispersed in the liquid with the reactant such that the reactant is located inside the microemulsion. Since the microemulsions of the present invention are stable the functionality of the reactants in the liquid is not affected when the nanoreactor is produced. The stability of the microemulsions of the present invention eliminates any need for a stabilization agent and the microemulsions of the present invention may be stable for over two weeks without any settling.

In an embodiment, the nanomaterials may be simultaneously generated and stabilized within the nanoreactor, which makes the nanoreactors a good nanomaterial carrier. In a further embodiment, the robustness of the microemulsion enables a wide array of reactants or chemicals to be placed in the resultant nanoreactor and allows the microemulsion to be used in a variety of harsh conditions including, but not limited to, alkalinity, acidity, and electrolyte concentration.

In another embodiment, chemicals or reactants that may be placed in the nanoreactor of the present invention include, but are not limited to, metal salts (e.g., ferric chloride, chloroauric acid, silver nitrate, ferrous oxide, copper salts, or zinc salts), metal oxides, carbon nanotubes, fullerenes, graphene, metal sulfides, metal alloys, metal composites, proteins, and/or reducing agents (e.g., sodium borohydride, sodium citrate, or green tea extract). Any combination of metal salts, oxidizing agents, and/or reducing agents may be used to produce nanomaterials using the nanoreactors of the present invention.

In another embodiment, a nanoparticle produced herein, may be used to produce a nanofluid which, optionally, may be diluted with a base fluid or solvent such as ethylene glycol, mineral oil, ethyl lactate, or other base fluid to produce the nanofluid. In an embodiment where ethyl lactate is used, the nanofluid may have utility in industrial and biomedical applications since ethyl lactate is biodegradable and biocompatible. In another embodiment, the base fluid may be an organic solvent that is biobased or petroleum based.

Lecithin is a lipid substance found in animal and plant tissues such as, for example, egg yolk, soybean, and canola or rapeseed. Lecithin includes various constituents including, but not limited to, phospholipids, such as, for example, phosphatidyl choline ("PC"), phosphatidyl inositol ("PI"), and phosphatidyl ethanolamine ("PE"). The amphophilic property of lecithin makes it an effective processing aid, emulsifier, dispersant and/or surfactant. Lecithin is also a natural ingredient than can form nanodispersions in aqueous mediums and carry high loads of actives. But, in such aqueous mediums, lecithin tends to have limited tolerance to pH and electrolytes.

Lecithin may be used, in applications where modification of the boundary layer between substances is desirable. In the presence of immiscible liquid phase, lecithin can reduce the interfacial surface tension and function as an emulsifier. When used with two or more solid phases, lecithin can function as a lubricant and/or release agent.

In one embodiment, a microemulsion used to produce the lecithin-based nanoreactor comprises a blend of lecithin and a co-surfactant, and an acidifier, where the lecithin is present at 10-90% by weight, the co-surfactant is present at 10-50% by weight, and the acidifier is present at 10-50% by weight. The microemulsion may further comprise a salt of the acidifier which may be present at 10-50% by weight, and in one embodiment, the microemulsion may have a pH of between 2-10.

Also, yet another embodiment of this invention describes a process for producing a microemulsion by mixing lecithin with a surfactant, thus forming a lecithin co-surfactant blend, and mixing an acidifier with the lecithin co-surfactant, thus forming a microemulsion. One aspect of this embodiment describes using vegetable fatty acids, soy fatty acids, derivatives of any thereof, and combinations of any thereof as additional components of the microemulsion that may be used to produce the lecithin-based nanoreactor.

In another embodiment, a lecithin-based microemulsion that is substantially biobased (is at least 95% biobased or at least 96% biobased) is disclosed. In one embodiment, the lecithin-based microemulsion complies with food grade requirements.

In a further embodiment, the lecithin-based microemulsion may be produced by incorporating a catalytic agent or precursors within reverse micelles that form from the lecithin-based microemulsion. When the reverse micelles contact each other upon simple mixing, the catalytic agents and precursors contact each other and spontaneously react to generate nanomaterials.

Microemulsions are clear, isotropic, thermodynamically stable liquid mixtures including oil, water and a surfactant. The water phase may contain salt(s) and/or other ingredients. In contrast to ordinary emulsions, microemulsions form upon simple mixing of the components and do not require high shear conditions. In ternary systems, such as microemulsions, where two immiscible phases (water and "oil") are present next to the surfactant phase, the surfactant molecules form a monolayer at the interface between oil and water, with the hydrophobic tails of the surfactant molecules dissolved in the oil phase and the hydrophilic head groups in the aqueous phase. Comparable to the binary systems (water/surfactant or oil/surfactant), self-assembled structures of different morphologies can be obtained ranging from (inverted) spherical and cylindrical micelles to lamellar phases and bi-continuous microemulsions. A water-in-oil microemulsion is an optically transparent mixture including oil, water, and surfactant. Water droplets are in a continuous oil phase stabilized by surfactant.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophihc-lipophilic balance value ranging from 10.0 to 24.0, and in certain embodiments 10.0 to 18.0.

The emulsifier and/or surfactant properties of an amphophilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No. 6,677,327, HLB is also described in Griffin, "Classification of Surface-Active Agents by HLB," *J. Soc. Cosmetic Chemists* 1 (1949); Griffin. "Calculation of HLB Values of Non-Ionic Surfactants," *J. Soc. Cosmetic Chemists* 5 (1954); Davies, "A quantitative kinetic theory of emulsion type, 1. Physical chemistry of the emulsifying agent," *Gas/liquid and Liquid/Liquid interfaces, Proceedings of the* 2d *International Congress on Surface Activity* (1957); and Schick, "Nonionic Surfactants: Physical Chemistry", Marcel Dekker, inc., New York, N.Y., pp. 439-47 (1987).

In various embodiments, the acidifier used in the disclosed compositions and methods may be selected from the group of acidifiers consisting of a lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, salts of any thereof, esters of any thereof, or combinations of any thereof. In another embodiment, the acidifier is selected from lactic acid, sodium lactate, ethyl lactate, or combinations of any thereof. The acidifier may also be a bio-derived acid, an organic acid, or a combination thereof. In another embodiment, a pH of the composition may be below 6, below 5, or below 4.

Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotope ratio or the $^{14}C/^{12}C$ carbon isotope ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D6866. ASTM international Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to be higher compared to bio-based products. In addition, companies may benefit from the marketing advantages associated with bio-derived products from renewable resources in the view of a public becoming more concerned with the supply of petrochemicals.

In various embodiments, the disclosed microemulsions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof. In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof. In various embodiments, the surfactant comprises a non-ionic surfactant, such as, for example, a fatty acid ethoxylate.

In another embodiment, the compositions of the present invention may be food grade and include a food grade surfactant such as, for example, a polysorbate.

The embodiments disclosed herein are also directed to methods or processes of preparing the disclosed compositions. In various embodiments, lecithin is mixed with a cosurfactant at ambient temperature and constantly stirred for a period of time. In another embodiment, an acidifier is added to the lecithin/co-surfactant blend at ambient temperature and mixed for a period of time. In another embodiment, water may be added after the acidifier is mixed with the lecithin/co-surfactant blend.

Other embodiments of the present invention, are directed towards uses of the microemulsions. The microemulsions may have uses including, but not limited to in bioremediation compositions; as delivery vehicles for nanomaterials such as nanoparticles, nanotubes, graphene, and graphite for delivery to base fluids such as metal working fluids, transformer fluids, and engine oil; as nano-delivery vehicles for materials such as bioactives, proteins, nutraceuticals, and pharmaceuticals in biomedical or cosmetic applications; as nanoreactors to carry out polymerization, synthesis, various reactions, and stabilization of monomers and/or oligomers for the synthesis of polymeric nanomaterials; making nanofluids for lubricating applications in heat transfer fluids, transformer fluids, or coolant additives; and making nanomaterials for coating applications.

EXAMPLES

The following exemplary, non-limiting examples are provided to further describe the embodiments presented herein. Those having ordinary skill in the art will appreciate that variations of these Examples are possible within the scope of the invention.

Example 1

A lecithin based microemulsion was produced with the ingredients of Table 1.

TABLE 1

| Ingredient | Amount |
|---|---|
| YELKIN T | 40.5% |
| Polysorbate 80 | 11.7% |
| Fatty acids | 3.5% |
| 88% strength lactic acid | 9.0% |
| Sodium lactate | 20.7% |
| Ethyl lactate | 14.6% |

To produce the microemulsion, a lecithin-cosurfactant blend was prepared by mixing the YELKIN T brand lecithin (available from Archer-Daniels-Midland Company of, Decatur, Ill.); a co-surfactant, polysorbate 80 (available from BASF, New Jersey); and fatty acids. The components were mixed at 50° C. under constant stirring for between 30 minutes to 60 minutes, thus producing an amber, transparent lecithin concentrate. The lecithin-cosurfactant blend is hydrophilic and easily dispersible in water.

The lecithin-cosurfactant blend was mixed with the sodium lactate (available from Archer-Daniels-Midland Company, Decatur, Ill.), followed by the 88% strength lactic acid (available from Archer-Daniels-Midland Company, Decatur, Ill.). To this blend, the ethyl lactate (available from Archer-Daniels-Midland Company, Decatur, Ill.) was added. The ingredients were constantly stirred for thirty minutes at room temperature to obtain a clear system that easily forms a stable, milky dispersion in water, thus forming the lecithin based microemulsion. In addition, the lecithin based microemulsion can solubilize additional water in an amount of up to 5-40% wt/wt and still maintain its clear and transparent microemulsion phase.

Example 2

A lecithin based microemulsion was produced with the ingredients of Table 2.

TABLE 2

| Ingredient | Amount |
|---|---|
| YELKIN T | 36% |
| Polysorbate 80 | 10.4% |
| Fatty acids | 3.2% |
| 88% strength lactic acid | 8% |
| Sodium lactate | 18.4% |
| Ethyl lactate | 4.0% |
| Mineral oil | 20.0% |

To produce the microemulsion, a lecithin-cosurfactant blend was prepared by mixing: the YELKIN T brand lecithin (available from Archer-Daniels-Midland Company of Decatur, Ill.); a co-surfactant, polysorbate 80 (available from BASF, New Jersey); and fatty acids. The components were mixed at 50° C. under constant stirring for between 30 minutes to 60 minutes, thus producing an amber, transparent lecithin concentrate. The lecithin-cosurfactant blend is miscible in mineral oil.

The lecithin-cosurfactant blend was mixed with the sodium lactate (available from Archer-Daniels-Midland Company, Decatur, Ill.), followed by the 88% strength lactic acid (available from Archer-Daniels-Midland Company, Decatur, Ill.). To this blend, the ethyl lactate (available from Archer-Daniels-Midland Company, Decatur, Ill.) was added. 80 g of this blend was mixed with 20 g mineral oil to form a microemulsion that was clear and transparent. This lecithin based, microemulsion is infinitely miscible in mineral oil. In addition, this lecithin based microemulsion can solubilize additional water in an amount of up to 5-40% wt/wt and still maintain its clear and transparent, microemulsion phase.

Example 3

The capacity of the microemulsion of Example 1 to encapsulate chemical entities was determined as follows. To 80 g of the microemulsion of Example 1, 11 g of $FeCl_3$ aqueous solution with varying ionic strengths were added and checked for phase inversion (i.e. conversion from microemulsion phase to typical emulsion phase) in the amounts presented in Table 3. As seen from Table 3, the encapsulation (or solubilization) capacity of the microemulsion of Example 1 is high and importantly independent of the concentration of the $FeCl_3$ in water. The only limitation is the solubility of $FeCl_3$ in water, which is 920 g/L or 3.41 M.

TABLE 3

| Microemulsion of Example 1 (% wt) | FeCl3 aqueous solution (%) | Strength of $FeCl_3$ solution (M) | Phase | Phase Inversion |
|---|---|---|---|---|
| 89 | 11 | 1 | Clear | No |
| 89 | 11 | 2 | Clear | No |
| 89 | 11 | 3 | Clear | No |
| 89 | 11 | 3.41 | Clear | No |

More importantly, the encapsulation capacity of the microemulsion was independent of the nature of the chemical entities dissolved in the water, thus demonstrating the encapsulation versatility of the microemulsion of Example 1. Since the microemulsion of Example 1 exhibited high encapsulation capacity towards $FeCl_3$, the microemulsions of the present invention would also have encapsulation capacity towards other metal salts including, but not limited to, $FeCl_2$, Fe(11) gluconate, $AgNO_3$, $HAuCl_4$, $CuSO_4$, and $ZnCl_2$, and reducing agents including, but not limited to, NaOH, $NaBH_4$, $Na_2S_2S_2O_6$, and Green tea extract. The microemulsions of the present invention may also be used to encapsulate many other water soluble/insoluble ingredients.

Example 4

The capacity of the microemulsion of Example 2 to encapsulate chemical entities was determined. To 89.2 g of the microemulsion of Example 2, 10.8 g of $FeCl_3$ aqueous solution with varying ionic strength was added and checked for the phase Inversion (i.e. conversion from microemulsion phase to typical emulsion phase) as shown in Table 4. As Table 4 indicates, the encapsulation (or solubilization) capacity of the microemulsion of Example 2 is high and importantly independent of the concentration of $FeCl_3$ in water. The only limitation is the solubility of $FeCl_3$ in water, which is 920 g/L or 3.41 M.

TABLE 4

| Microemulsion of Example 1 (% wt) | FeCl3 aqueous solution (%) | Strength of FeCl3 solution (M) | Phase | Phase Inversion |
|---|---|---|---|---|
| 89 | 11 | 1 | Clear | No |
| 89 | 11 | 2 | Clear | No |
| 89 | 11 | 3 | Clear | No |
| 89 | 11 | 3.41 | Clear | No |

More importantly, the encapsulation capacity was independent of the nature of the chemical entities dissolved in the water, thus, demonstrating the encapsulation versatility of the microemulsion of Example 2.

Since the microemulsion of Example 2 exhibited high encapsulation capacity towards $FeCl_3$, the microemulsions of the present invention would also have encapsulation capacity towards other metal salts including, but not limited to, $FeCl_2$, Fe(11) gluconate, $AgNO_3$, $HAuCl_4$, $CuSO_4$, and $ZnCl_2$, and reducing agents including, but not limited to, NaOH, $NaBH_4$, $Na_2S_2O_6$, and Green tea extract. The microemulsions of the present invention may also be used to encapsulate many other water soluble/insoluble ingredients.

Example 5

In this embodiment, the water in oil lecithin based microemulsion of Example 1 was used to encapsulate a chelating agent and develop a formulation, which can be used for chelating formulation. To 89 g of the microemulsion of Example 1, 11 g of a saturated solution of EDETA® brand aminocarboxylic acid (available from BASF of North America) was dissolved. The resulting mixture was clear and transparent, indicative of the solubilization of water and encapsulation of chelating agent within the reverse micelles. Such formulations can be used as such or after being dispersed in water, in applications requiring chelation of metal ions and simultaneously stabilize the metal ions against precipitation from the end solution.

Example 6

In this embodiment, the water in oil lecithin based microemulsion of Example 2 was used to encapsulate a chelating agent and develop a formulatlon, which can be used for chelating formulation. To 89.2 g of the microemulsion of Example 2, 10.8 g of saturated solution of EDETA® brand aminocarboxylic acid (available from BASF of North America) was dissolved. The resulting mixture was clear and transparent, indicative of solubilization of water and encapsulation of chelating agent within the reverse micelles. Such formulations can be used as such or after being dispersed in water, in applications requiring chelation of metal ions and simultaneously stabilize the metal ions against precipitation from the end solution.

Example 7

In this embodiment, the water in oil lecithin based microemulsion of Example 1 was used to create a nanomaterial by mixing two reactants. Two microemulsions were prepared, microemulsion A included 80 g of the lecithin based microemulsion of Example 1 mixed with 20 g of 1 M $FeCl_3$ aqueous solution and microemulsion B included 80 g of the lecithin based microemulsion of Example 1 mixed with 20 g of a green tea extract (GTE) aqueous solution (5% wt/v).

20 g of microemulsion A was slowly added to 80 g of microemulsion B (i.e., a ration of A:B of 1:4). Upon mixing of the two solutions, the reducing agent (i.e., the polyphenols in the green tea extract) reduced the $Fe^{3+}$ ions resulting in the formation of nanoparticles of $Fe^0$ which was visualized by the blackening of the microemulsion solution. If desired, the $Fe^0$ nanoparticle within the microemulsion containing the ethyl lactate could be further diluted with ethyl lactate to a desired concentration without losing the nanoparticle stabilization functionality of the microemulsion. The nanoparticles are encapsulated and stabilized within the core of reverse micelles. The nanoparticles in this Example were found to be stable over several weeks, whereas nanoparticles prepared in water (without microemulsion) aggregated and precipitated out of solution within a day. The lecithin and polysorbate, which constitute the micellar core, impart steric and electrostatic stabilization, thus inhibiting the agglomeration of the nanoparticles.

Studies were done to determine the concentrations of $FeCl_3$ and green tea extract that optimally produced nanoparticles. Optimum concentrations were determined to ensure complete conversion of ions to nanoparticles and maximize loading of nanoparticles without sacrificing their stability, $FeCl_3$ was varied in aqueous solution between 0.5 to 1.0 M and the green tea extract was varied in aqueous solution between 1% to 5% wt/v. The ratios of $FeCl_3$ to green tea extract was varied from 1:4, 1:1, and 4:1. It was found that a 1 M $FeCl_3$ concentration, a 5% green tea extract concentration, and a $FeCl_3$ to green tea extract concentration of 1:4 produced the best result. The higher concentration of green tea extract had an excess amount of the reducing agent (i.e., polyphenols) which helped ensure the complete reduction of all of the $Fe^{3+}$ ions to the $Fe^0$ nanoparticle. In another embodiment, gold and silver nanoparticles could also be prepared using the process of this Example.

Example 8

The water in oil lecithin based microemulsion of Example 1 was used to create a nanomaterial by mixing 80 g of the lecithin based microemulsion of Example 1 mixed with 4 g of 1 M $FeCl_3$ aqueous solution. To this microemulsion blend, 16 g of a green tea extract (GTE) aqueous solution (5% wt/v) was slowly added to produce $Fe^0$ nanoparticles. This method differed from Example 5 in that Example 5 prepared two different microemulsions for each reactant, while Example 6 used one microemulsion. However, both the methods in Example 5 and Example 6 produced the desired nanoparticles.

Example 9

In another embodiment, microemulsion A was formed by mixing 89.9 g of the microemulsion of Example 1 with 10.1 g of 1 mM $AgNO_3$ aqueous solution and microemulsion B was formed, by mixing 89.9 g of the microemulsion of Example 1 with 10.1 g of a 4% (wt/v) green tea extract aqueous solution. Microemulsion A was slowly mixed into the microemulsion B in 1:4 proportion, resulting in formation of $Ag^0$ nanoparticle within the microemulsion. If desired, the $Ag^0$ nanoparticle within the microemulsion containing the ethyl lactate could be further diluted with ethyl lactate to a desired concentration without losing the nanoparticle stabilization functionality of the microemulsion. The nanoparticles were encapsulated and stabilized within the core of reverse micelles. The nanoparticles in this Example were found to be stable over several weeks, whereas nanoparticles prepared in water (without microemulsion) aggregated and precipitated out of solution within a day. The lecithin and polysorbate, which constitute the micellar core, impart steric and electrostatic stabilization, thus inhibiting the agglomeration of the nanoparticles.

Example 10

In another embodiment microemulsion A was formed by mixing 89.9 g of the microemulsion of Example 1 with 10.1 g of 1 mM $HAuCl_4$ aqueous solution and microemulsion B was formed by mixing 89.9 g of microemulsion of Example 1 with 10.1 g of a 4% (wt/v) green tea extract aqueous solution. Microemulsion A was mixed into the microemulsion B in 1:4 proportion, resulting in formation of $Au^0$ nanoparticle within the microemulsion as evidenced by a purple colored solution. If desired, the $Au^0$ nanoparticle within the microemulsion containing the ethyl lactate could be further diluted with ethyl lactate to a desired concentration without losing the nanoparticle stabilization functionality of the microemulsion. The nanoparticles were encapsulated and stabilized within the core of reverse micelles. The nanoparticles in this Example were found to be stable over several weeks, whereas nanoparticles prepared in water (without microemulsion) aggregated and precipitated out of solution within a day. The lecithin and polysorbate, which constitute the micellar core, impart steric and electrostatic stabilization, thus inhibiting the agglomeration of the nanoparticles.

Example 11

Iron sulfide nanoparticles were synthesized using the water in oil lecithin based microemulsion of Example 1. At first 90 g of the microemulsion of Example 1 was thoroughly mixed with 10 g of 0.3 M $FeCl_3$ solution. The added $FeCl_3$ molecules were encapsulated inside the reverse of micelle of microemulsion. To the resulting microemulsion, 10 g of reducing agent was added dropwise at which point the solution turned black indicative of formation of iron sulfide, FeS. The reducing agent included a mixture of $NaBH_4$ (5.64% wt) and $Na_2S_2O_6$ (0.469% wt) dissolved in water. The nanoparticles were encapsulated and stabilized within the core of reverse micelles. The nanoparticles in this Example were found to be stable over several weeks, whereas nanoparticles prepared in water (without microemulsion) aggregated and precipitated out of solution within a day. The lecithin and polysorbate, which constitute the micellar core, impart steric and electrostatic stabilization, thus inhibiting the agglomeration of the nanoparticles.

Example 12

In addition to the process described in Example 11, iron sulfide particles can be synthesized in an additional method, which may be used in drilling technology. 10 g of a microemulsion including 90 g of the microemulsion of Example 1 and 10 g of 0.3 M $FeCl_3$ was dispersed in 90 g of deionixed water. The dispersion resulted in phase inversion, i.e. a clear water-in-oil microemulsion was converted in oil-in-water emulsion. To this emulsion, 5.4 g of a reducing agent was added, which included a mixture of $NaBH_4$ (5.64% wt) and $Na_2S_2O_6$ (0.469% wt) dissolved in water. On addition of the reducing agent, the reaction mixture formed thick blackish foam and the solution changed from a light yellow color to grayish, black color, indicative of formation of iron sulfide, FeS.

Immediately after formation of the FeS particles, the emulsion's amphophilic constituents such as lecithin, lactic acid and polysorbate are adsorbed on the particle at the solid-liquid interface. The amphiphilic adsorption imparts steric and electrostatic stabilization of particle, thus inhibiting their agglomeration and eventual precipitation.

Example 13

As demonstrated in Example 12, the microemulsion (which is a mixture of 89% of microemulsion of Example 1 and 11% $FeCl_3$) when contacted with a sulfur donating reagent (sodium dithionate) results in immediate conversion of $Fe^{3+}$ to iron sulfide, indicative of rapid reaction. The microemulsion is extremely stable over a wide range of pH (2-14) and no destabilization of emulsion structure was observed over a period of two weeks when the microemulsion was dispersed in water with a pH ranging from 2 to 14. The iron sulfide formed after the reaction remains suspended within the system. The composition of the microemulsion, especially microemulsion of example 1, complies with food grade requirements. All these attributes are prerequisites for a material which is to be used as hydrogen sulfide scavenger for drilling fluids. Hence, the microemulsion can be used as a thinner as well as an iron delivery vehicle in water-based drilling fluids. The iron delivery vehicles will act as sulfide scavengers for the drilling fluids.

Example 14

In this embodiment, the water in oil lecithin based microemulsion of Example 2 was used to create a nanomaterial by mixing two reactants. A first microemulsion was formed by mixing 89.2 g of the microemulsion of Example 2 with 10.8 g of 1 M $FeCl_3$ aqueous solution. A second microemulsion was formed by mixing 89.2 g of microemulsion of Example 4 with 10.8 g of a 4% (wt/v) green tea extract aqueous solution.

The first microemulsion was mixed into the second microemulsion in 1:4 proportion, resulting in $Fe^0$ nanoparticle within the microemulsion as evidenced by a black colored solution. The resulting $Fe^0$ nanoparticle within the microemulsion containing the mineral oil could be used in a nanofluid system. If desired, the $Fe^0$ nanoparticle within the microemulsion containing the mineral oil could be former diluted with mineral oil to a desired concentration without losing the nanoparticle stabilization functionality of the microemulsion.

Example 15

The microemulsions of the present invention were found to be stable and stay in solution after two weeks. $Fe^0$ nanoparticles generated in an ethyl lactate containing microemulsion and in a mineral oil containing microemulsion were produced in accordance with the present invention. For comparison, bulk nanoparticles were prepared by mixing the water phases of $FeCl_3$ and green tea extract, which were not encapsulated in a microemulsion of the present invention. Visual inspection of the $Fe^0$ nanoparticles in the ethyl lactate microemulsion. the mineral oil microemulsion, and the bulk nanoparticles indicated that the microemulsions of the present invention were able to stabilize the nanoparticles for over two weeks where no settling was observed. In the case of the bulk nanoparticles, the nanoparticles aggregated and precipitated out of solution within a day. The nanoparticles were encapsulated and stabilized within the core of reverse micelles. The lecithin and polysorbate, which constitute the micellar core, impart steric and electrostatic stabilization, thus inhibiting the agglomeration of the nanoparticles.

Example 16

A first microemulsion was formed by mixing 89.2 g of the microemulsion of Example 2 with 10.8 g of 1 mM $AgNO_3$ aqueous solution. A second microemulsion was formed by mixing 89.2 g of the microemulsion of Example 4 with 10.8 g of a 4% (wt/v) green tea extract aqueous solution. The first microemulsion was mixed into the second microemulsion in 1:4 proportion, resulting in formation of $Ag^0$ nanoparticle within the microemulsion. If desired, the $Ag^0$ nanoparticle within the microemulsion containing the ethyl lactate could be further diluted with ethyl lactate to a desired concentration without losing the nanoparticle stabilization functionality of the microemulsion. The nanoparticles were encapsulated and stabilized within the core of reverse micelles. The lecithin and polysorbate, which constitute the micellar core, impart steric and electrostatic stabilization, thus inhibiting the agglomeration of the nanoparticles.

Example 17

A first microemulsion was formed by mixing 89.2 g of the microemulsion of Example 2 with 10.8 g of 1 mM $HAuCl_4$ aqueous solution. A second microemulsion was formed by mixing 89.2 g of the microemulsion of Example 4 with 10.8 g of a 4% (wt/v) green tea extract aqueous solution. The first microemulsion was mixed into the second microemulsion in 1:4 proportion, resulting in formation of $Au^0$ nanoparticle within the microemulsion as evidenced by purple color solution. If desired, the $Au^0$ nanoparticle within the microemulsion containing the ethyl lactate could be further diluted with ethyl lactate to a desired concentration without losing the nanoparticle stabilization functionality of the microemulsion. The nanoparticles were encapsulated and stabilized within the core of reverse micelles. The lecithin and polysorbate, which constitute the micellar core, impart steric and electrostatic stabilization, thus inhibiting the agglomeration of the nanoparticles.

Example 18

A lecithin based microemulsion was produced with the ingredients of Table 5.

TABLE 5

| Ingredient | Amount |
| --- | --- |
| YELKIN T brand lecithin | 36% |
| Polysorbate 80 | 10.4% |
| Fatty acids | 3.2% |
| 88% strength lactic acid | 8.0% |
| Sodium lactate | 18.4% |
| Ethyl lactate | 24% |

To produce the microemulsion, a lecithin-cosurfactant blend was prepared by mixing: the YELKIN T brand lecithin (available from Archer-Daniels-Midland Company of Decatur, Ill.); a co-surfactant, polysorbate 80 (available from BASF, New jersey); and fatty acids. The components were mixed at 50° C. under constant stirring for between 30 minutes to 60 minutes, thus producing an amber, transparent lecithin concentrate. The lecithin-cosurfactant blend is hydrophilic and easily dispersible in water.

The lecithin-cosurfactant blend was mixed with the sodium lactate (available from Archer-Daniels-Midland Company, Decatur, Ill.), followed by the 88% strength lactic acid (available from Archer-Daniels-Midland Company, Decatur, Ill.). To this blend, the ethyl lactate (available from Archer-Daniels-Midland Company, Decatur, Ill.) was added. The ingredients were constantly stirred for thirty minutes at room temperature to obtain a clear system that easily forms a stable, milky dispersion in water, thus forming the lecithin based microemulsion. In addition, the lecithin based microemulsion can solubilize additional water in an amount of up to 5-40% wt/wt and still maintain its clear and transparent microemulsion phase.

Example 19

In this embodiment, the water in oil lecithin based microemulsion of Example 18 was used to create a nanomaterial by mixing two reactants. A first microemulsion was formed by mixing 83.3 g of the microemulsion of Example 18 with 16.7 g of 1.5 M $FeCl_3$ aqueous solution. A second microemulsion was formed by mixing 80.0 g of microemulsion of Example 18 with 20.0 g of a 5% (wt/v) green tea extract aqueous solution.

The first microemulsion was mixed into the second microemulsion in 2:1 proportion, resulting in $Fe^0$ nanoparticle within the microemulsion as evidenced by a black colored solution. The net concentration of $Fe^0$ in the resulting microemulsion would be 4.3% wt. The particle size of $Fe^0$ particles present in the microemulsion was in the range of 8-12 nm which was determined by using Cryo-TEM. The resulting $Fe^0$ nanoparticle within the microemulsion containing the ethyl lactate could be used in a nanofluid/bioremediation system. If desired, the $Fe^0$ nanoparticle within the microemulsion containing the ethyl lactate could be further diluted with ethyl lactate to a desired concentration without losing the nanoparticle stabilization functionality of the microemulsion.

Example 20

The first microemulsion of Example 19 (microemulsion with 1.5 M $FeCl_3$) was mixed into the second microemulsion of Example 19 (5% (wt/v) green tea extract) in 1:1 proportion, resulting in $Fe^0$ nanoparticle within the microemulsion as evidenced by a black colored solution. The net concentration of $Fe^0$ in the resulting microemulsion would be 3.6% wt. The resulting $Fe^0$ nanoparticle within the microemulsion containing the ethyl lactate could be used in a nanofluid/bioremediation system. If desired, the $Fe^0$ nanoparticle within the microemulsion containing the ethyl lactate could be further diluted with ethyl lactate to a desired concentration without losing the nanoparticle stabilization functionality of the microemulsion.

Example 21

In this embodiment, the water in oil lecithin based microemulsion of Example 18 was used to create a nanomaterial by mixing two reactants. A first microemulsion was formed by mixing 83.3 g of the microemulsion of Example 18 with 16.7 g of 1.5 M FeCl₃ aqueous solution. A second microemulsion was formed by mixing 80.0 g of microemulsion of Example 18 with 20.0 g of a 10% (wt/v) green tea extract aqueous solution.

The first microemulsion was mixed into the second microemulsion in 2:1 proportion, resulting in $Fe^0$ nanoparticle within the microemulsion as evidenced by a black colored solution. The net concentration of $Fe^0$ in the resulting microemulsion would be 4.3% wt. The resulting $Fe^0$ nanoparticle within the microemulsion containing the ethyl lactate could be used in a nanofluid/bioremediation system. If desired, the $Fe^0$ nanoparticle within the microemulsion containing the ethyl lactate could be further diluted with ethyl lactate to a desired concentration without losing the nanoparticle stabilization functionality of the microemulsion.

Example 22

The first microemulsion of Example 21 (microemulsion with 1.5 M FeCl₃) was mixed into the second microemulsion of Example 21 (10% (wt/v) green tea extract) in 1:1 proportion, resulting in $Fe^0$ nanoparticle within the microemulsion as evidenced by a black colored solution. The net concentration of $Fe^0$ in the resulting microemulsion would be 3.6% wt/wt. The resulting $Fe^0$ nanoparticle within the microemulsion containing the ethyl lactate could be used in a nanofluid/bioremediation system. If desired, the $Fe^0$ nanoparticle within the microemulsion containing the ethyl lactate could be further diluted with ethyl lactate to a desired concentration without losing the nanoparticle stabilization functionality of the microemulsion.

Example 23

In addition to in situ generation of a nanomaterial within the micellar structure of microemulsions described herein, externally made nanomaterials can also be encapsulated and stabilized within the micellar structure of the microemulsions described herein.

A lecithin based microemulsion was produced with the ingredients of Table 6.

TABLE 6

| Ingredient | Amount |
|---|---|
| YELKIN T brand lecithin | 45% |
| Polysorbate 80 | 13% |
| Fatty acids | 4% |
| 88% strength lactic acid | 10% |
| Sodium lactate | 23% |
| Ethyl lactate | 5% |

This lecithin-based microemulsion can be prepared by the procedure substantially as described in Example 1. In addition, the lecithin based microemulsion can solubilize additional water (5-40% wt/wt) and/or ethyl lactate (0.1-50% wt/wt and still maintain its clear and transparent microemulsion phase.

Example 24

The water in oil lecithin based microemulsion of Example 23 was used to encapsulate and stabilize an externally prepared nanomaterial. A 10% wt/wt slurry of zinc oxide nanopowder (<100 nm, from Sigma Aldrich) in ethyl lactate was prepared. 20 g of the slurry was added to 80 g of the microemulsion of Example 23. The mixture was stirred until all of the zinc oxide nanopowder was encapsulated resulting into a clear and transparent microemulsion. The zinc oxide nanopowder was stabilized in the microemulsion as it did not show any sign of precipitation after two weeks. The net concentration of zinc oxide in the resulting microemulsion would be 2% wt/wt. The resulting microemulsion containing the encapsulated nanomaterial can be used for numerous applications like cosmetics, pharmaceutics, biomedical etc. In addition, the microemulsion containing the ethyl lactate and encapsulated zinc oxide nanopowder could be further diluted with ethyl lactate/water to a desired concentration without losing the nanoparticle stabilization functionality of the microemulsion.

Example 25

This example demonstrates that the nanomaterial can be encapsulated within the micellar structure simultaneously while making the microemulsion itself. A lecithin based microemulsion was produced with the ingredients of Table 7.

TABLE 7

| Ingredient | Amount |
|---|---|
| YELKIN T brand lecithin | 44.1% |
| Polysorbate 80 | 12.74% |
| Fatty acids | 3.92% |
| 88% strength lactic acid | 9.8% |
| Sodium lactate | 22.54% |
| ZnO Nanopowder (<100 nm) | 2 |
| Ethyl lactate | 4.9% |

A lecithin-cosurfactant blend, was prepared by mixing: the YELKIN T brand lecithin (available from Archer-Daniels-Midland Company of, Decatur, Ill.); a co-surfactant, polysorbate 80 (available from BASF, New Jersey); and fatty acids. The components were mixed at 50° C. under constant stirring for between 30 minutes to 60 minutes, thus producing an amber, transparent lecithin concentrate. The lecithin-cosurfactant blend is hydrophilic and easily dispersible in water.

A clear blend of sodium lactate (available from Archer-Daniels-Midland Company, Decatur, Ill.), 88% strength lactic acid (available from Archer-Daniels-Midland Company, Decatur, Ill.) and ZnO nanopowder (available from Sigma Aldrich, <100 nm) was prepared by mixing. The blend was mixed with the lecithin-cosurfactant blend. To this ethyl lactate (available from Archer-Daniels-Midland Company, Decatur, Ill.) was added. The ingredients were constantly stirred for thirty minutes at room temperature to obtain a clear system that easily forms a stable, milky dispersion in water, thus forming the lecithin based nanomaterial containing microemulsion. In addition, the microemulsion containing the ethyl lactate and encapsulated zinc oxide nanopowder could be further diluted with ethyl lactate/water to a desired concentration without losing the nanoparticle stabilization functionality of the microemulsion.

Examples 24 and 25 demonstrate that premade nanomaterials can be encapsulated in lecithin-based microemulsions of the present invention. The nanomaterial can be encapsulated after the microemulsion is made or encapsulated during the process used to make the microemulsion.

This disclosure has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A method of encapsulating a nanomaterial in a lecithin based microemulsion, the method comprising:
mixing the lecithin based microemulsion with the nanomaterial, thus encapsulating and stabilizing the nanomaterial; wherein the lecithin based microemulsion comprises:
10-90% by weight lecithin:
a co-surfactant;
fatty acids;
a carboxylic acid;
a salt of the carboxylic acid;
an ester of the carboxylic acid; and
water;
wherein the nanomaterial is selected from the group consisting of activated carbon, carbon nanofibers, carbon nanoplatelets, carbon nanotubes, fullerenes, graphene, graphene nanopowder, graphene nanoplatelets, graphene oxide fullerenes, and combinations of any thereof.

2. The method of claim 1, wherein the nanomaterial has a particle size of between 2-500 nanometers.

3. The method of claim 1, wherein the nanomaterial within the lecithin based microemulsion has a particle size of between 5-50 nanometers.

4. The method according to claim 1, wherein the carboxylic acid is selected from the group consisting of lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, and combinations of any thereof.

5. The method according to claim 1, wherein the carboxylic acid is lactic acid, the salt of the carboxylic acid is sodium lactate, and the ester of the carboxylic acid is ethyl lactate.

6. The method according to claim 1, further comprising dispersing the lecithin based microemulsion in a non-polar solvent selected from the group consisting of non-polar organic solvents, ionic liquids, vegetable oil, mineral oil, an essential oil, paraffin, petroleum fractions, and combinations of any thereof.

* * * * *